(12) United States Patent
Nguyen

(10) Patent No.: US 10,517,697 B2
(45) Date of Patent: Dec. 31, 2019

(54) DECORATIVE COVERS FOR DENTAL BRACES

(71) Applicant: Bracees, LLC, Newark, OH (US)

(72) Inventor: Sy Viet Nguyen, Newark, OH (US)

(73) Assignee: Bracees, LLC, Newark, OH (US)

( * ) Notice: Subject to any disclaimer, the term of this patent is extended or adjusted under 35 U.S.C. 154(b) by 255 days.

(21) Appl. No.: 14/947,375

(22) Filed: Nov. 20, 2015

(65) Prior Publication Data

US 2017/0035532 A1 Feb. 9, 2017

Related U.S. Application Data

(60) Provisional application No. 62/201,332, filed on Aug. 5, 2015.

(51) Int. Cl.
A61C 7/12 (2006.01)
A61C 7/14 (2006.01)
A61C 7/20 (2006.01)
A61C 7/28 (2006.01)

(52) U.S. Cl.
CPC .............. A61C 7/125 (2013.01); A61C 7/12 (2013.01); A61C 7/14 (2013.01); A61C 7/20 (2013.01); A61C 7/28 (2013.01); A61C 2203/00 (2013.01)

(58) Field of Classification Search
CPC .................................. A61C 7/125; A61C 7/12
USPC ........................................ 433/8, 10, 11, 13
See application file for complete search history.

(56) References Cited

U.S. PATENT DOCUMENTS

| 3,052,028 | A | * | 9/1962 | Wallshein | A61C 7/30 433/11 |
| 4,023,274 | A | * | 5/1977 | Wallshein | A61C 7/30 433/11 |
| 4,180,912 | A | * | 1/1980 | Kesling | A61C 7/12 327/437 |
| 4,527,975 | A | * | 7/1985 | Ghafari | A61C 7/125 433/8 |
| 6,142,775 | A | * | 11/2000 | Hansen | A61C 7/12 433/14 |
| 6,168,429 | B1 | | 1/2001 | Brown | |
| 7,303,220 | B2 | * | 12/2007 | Zellak | G02B 6/3807 29/762 |
| 2006/0257808 | A1 | * | 11/2006 | Feller | A61C 7/00 433/2 |
| 2013/0196281 | A1 | * | 8/2013 | Thornton | A61C 13/26 433/8 |

(Continued)

Primary Examiner — Yogesh P Patel
Assistant Examiner — Stephen R Sparks
(74) Attorney, Agent, or Firm — Porter, Wright, Morris & Arthur, LLP

(57) ABSTRACT

A cover for an orthodontic bracket having an arch wire laterally extending therethrough includes a body having a forward-facing planar surface and a rearward-facing recess configured for at least partially receiving the orthodontic bracket therein. The body includes first and second slots located on opposed lateral sides of the body and each configured so that the arch wire passes laterally through the first and second slots and the recess of the body when the cover is positioned over the orthodontic bracket. The forward-facing planar surface is provided with decorative indicia thereon. The cover is configured so that the cover does not bind movement of the arch wire relative to the orthodontic bracket, does not secure the arch wire to the orthodontic brackets, and does not alter the functioning of the dental braces.

12 Claims, 17 Drawing Sheets

(56) References Cited

U.S. PATENT DOCUMENTS

2014/0212828 A1\* 7/2014 Falcone .................. A61C 7/14
433/11

\* cited by examiner

DECORATIVE COVERS FOR DENTAL BRACES

CROSS-REFERENCE TO RELATED APPLICATIONS

This application claims the priority benefit of U.S. provisional patent application No. 62/201,332 filed on Aug. 5, 2015, the disclosure of which is expressly incorporated herein in its entirety by reference.

STATEMENT REGARDING FEDERALLY SPONSORED RESEARCH

Not Applicable

PARTIES TO A JOINT RESEARCH AGREEMENT

Not Applicable

REFERENCE TO APPENDIX

Not Applicable

FIELD OF THE INVENTION

The field of the present invention generally relates to dental braces and, more particularly, to covers for dental braces.

BACKGROUND OF THE INVENTION

Dental or orthodontic braces, also known as dental or orthodontic cases, are devices used in orthodontics that align and straighten teeth and help position the teeth with regard to a person's bite, while also working to improve dental health. Dental braces are often used to correct under bites, as well as malocclusions, overbites, open bites, deep bites, cross bites, crooked teeth, and/or various other flaws of the teeth and jaw.

The application of dental braces to teeth moves the teeth as a result of force and pressure on the teeth. There are typically four basic components of dental braces: brackets for pressuring the teeth in a desire d direction, bonding material for bonding the brackets to the teeth, arch wire extending between the brackets, and ligatures (often elastic "O-rings" or bands) for holding the arch wire to the brackets. The teeth move when the arch wire puts pressure on the brackets and teeth. Sometimes springs or rubber bands are used to put more force in a specific direction. The dental braces apply constant pressure which, over time, moves the teeth into desired positions. Traditional metal braces are the most common type of dental braces. These dental braces have a metal bracket with elastic ligatures (rubber bands) holding the metal arch wire onto the metal brackets. Traditional metal braces are stainless steel and are sometimes used in combination with titanium. The second most common type of braces is self-ligating braces that do not require the elastic ligatures. Instead, the metal arch wire goes through the metal bracket so it is held to the bracket by the bracket itself or a bracket insert.

While many people need to have their teeth aligned and straightened, dental braces can negatively impact on how a person feels about oneself. Image is important at any age, but for many children, tweens, and/or teens who are at an already delicate period of self-esteem, the thought of having brackets and wires attached to their teeth exacerbates self-esteem issues. A national survey suggests that over one-half of teens believe metal braces would make them more self-conscious and one-half of teens would smile less. In order to lessen the impact of these metal braces on self-image, cosmetic alternatives to metal braces have been pursued that attempt to "hide" the braces. Clear or transparent dental braces serve as a cosmetic alternative to metal braces by blending in with the natural color of the teeth or having a less conspicuous or hidden appearance. Lingual braces are a cosmetic alternative in which custom-made dental braces are bonded to the back of the teeth making them externally invisible. Progressive, removable aligners (examples of which are Invisalign, Originator, and ClearCorrect) are an alternative to dental braces and are hardly noticeable on the teeth because they are clear. These aligners work to gradually move the teeth into their desired positions without the need for wires or tightening. While these cosmetic alternatives to metal braces may be somewhat successful at improving self-image, these cosmetic alternatives do not work in all applications and/or can be much more costly than metal braces.

With regard to children, tweens and teens, an alternative approach to lessen the impact of dental braces on self-image has been to decorate or personalize their dental braces by letting them select a favorite color or colors for archwires and/or ligatures. For example, a patient could choose to have a purple archwire with yellow rubber bands at one adjustment so that the braces appear more stylish and then switch to pink rubber bands at the next adjustment so that they have a new and different stylish look. While this may be somewhat successful at improving self-image, it has relatively limited ability to personalize the dental braces. Currently, wearers of dental braces are otherwise unable to express themselves by personalizing and/or decorating their braces. Accordingly, there is a need in the art for improved systems and methods for personalizing and/or decorating their dental braces.

SUMMARY OF THE INVENTION

Disclosed are covers for orthodontic brackets of dental braces that overcome at least one of the disadvantages of the prior art described above. Disclosed is a cover for an orthodontic bracket having an arch wire laterally extending therethrough. The cover comprises a body having a forward-facing surface and a rearward-facing recess configured for at least partially receiving the orthodontic bracket therein. The body includes first and second slots located on opposed lateral sides of the body and each configured so that the arch wire passes laterally through the first and second slots and the recess of the body.

Also disclosed are dental braces comprising, in combination, at least one orthodontic bracket for securement to a tooth and having a laterally-extending slot, an arch wire extending laterally through the slot of the orthodontic bracket, and a cover. The cover comprises a body having a forward-facing surface and a rearward-facing recess configured for at least partially receiving the orthodontic bracket therein. The body includes first and second slots located on opposed lateral sides of the body and each configured so that the arch wire passes through the first and second slots and the recess of the body.

Also disclosed is a method of covering an orthodontic bracket having an arch wire laterally extending therethrough. The method comprises the steps of obtaining a cover comprising a body having a forward-facing surface and a rearward-facing recess configured for at least partially receiving the orthodontic bracket therein. The body includes first and second slots located on opposed lateral sides of the body and each configured so that the arch wire passes laterally through the first and second slots and the recess of the body. The method further comprises the step of moving the body over the orthodontic bracket so that the arch wire moves into the first and second slots and the orthodontic bracket is at least partially received in the recess and the cover covers at least a front side of the orthodontic bracket.

From the foregoing disclosure and the following more detailed description of various preferred embodiments it will be apparent to those skilled in the art that the present invention provides a significant advance in the technology and art of dental braces. Particularly significant in this regard is the potential the invention affords for a cover that is disposable, relatively inexpensive, and effective at personalizing and/or decorating orthodontic brackets of dental braces. Additional features and advantages of various preferred embodiments will be better understood in view of the detailed description provided below.

BRIEF DESCRIPTION OF THE DRAWINGS

These and further features of the present invention will be apparent with reference to the following description and drawing, wherein.

Figure 1:
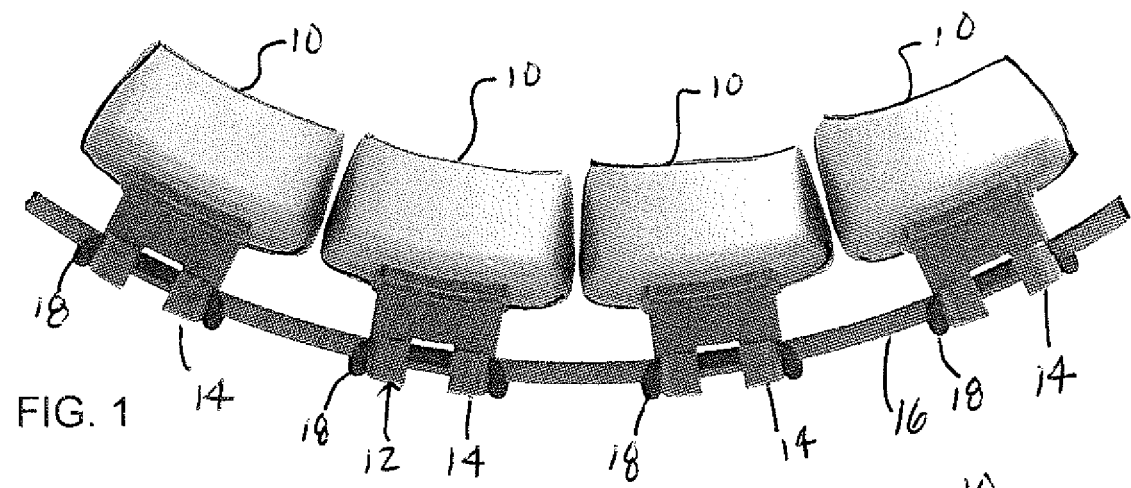
FIG. 1 is a top view of a plurality of teeth with dental braces secured thereto.

It should be understood that the appended drawings are not necessarily to scale, presenting a somewhat simplified representation of various preferred features illustrative of the basic principles of the invention. The specific design features of the bracket cover as disclosed herein, including, for example, specific dimensions and shapes of the various components will be determined in part by the particular intended application and use environment. Certain features of the illustrated embodiments have been enlarged or distorted relative to others to facilitate visualization and clear understanding. In particular, thin features may be thickened, for example, for clarity or illustration. All references to direction and position, unless otherwise indicated, refer to the orientation of the vibration isolation systems illustrated in the drawings. In general, up or upward refers to an upward direction generally within the plane of the paper in FIG. 8 and down or downward refers to a downward direction generally within the plane of the paper in FIG. 8. Also in general, forward or front refers to a direction extending out of the plane of the paper in FIG. 8 and back or rear refers to a direction extending into the plane of the paper in FIG. 8.

DETAILED DESCRIPTION OF CERTAIN PREFERRED EMBODIMENTS

It will be apparent to those skilled in the art, that is, to those who have knowledge or experience in this area of technology, that many uses and design variations are possible for the covers for orthodontic brackets of dental braces disclosed herein. The following detailed discussion of various alternative and preferred embodiments will illustrate the general principles of the invention with regard to the specific application of a cover for dental braces having metal twin brackets. Other embodiments suitable for other applications such as, for example, dental braces having self-ligating brackets, will be apparent to those skilled in the art given the benefit of this disclosure.

Figure 2:
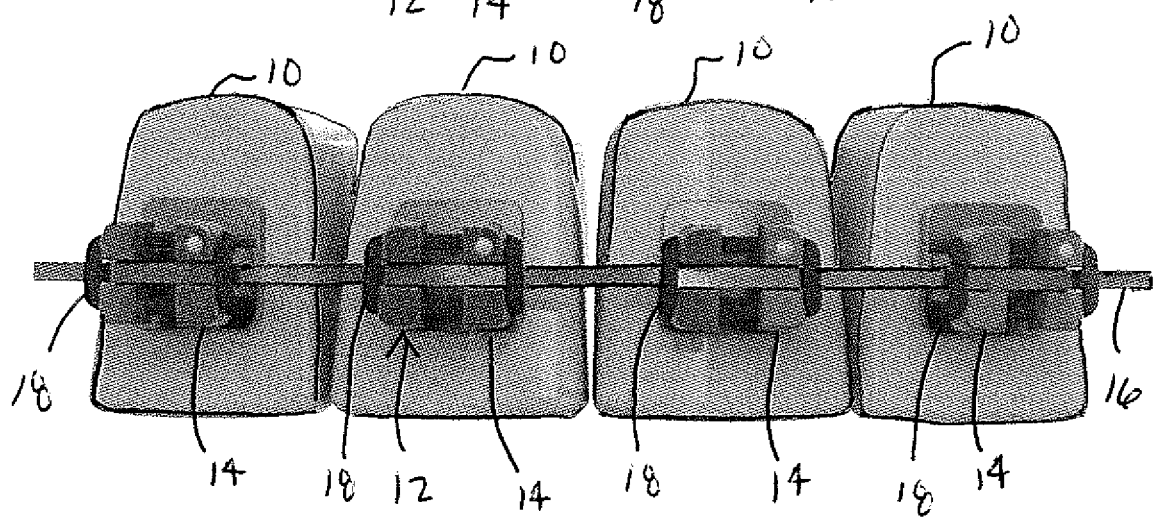
FIG. 2 is a front elevational view of the plurality of teeth of FIG. 1 with the metal dental braces secured thereto.
Figure 4:
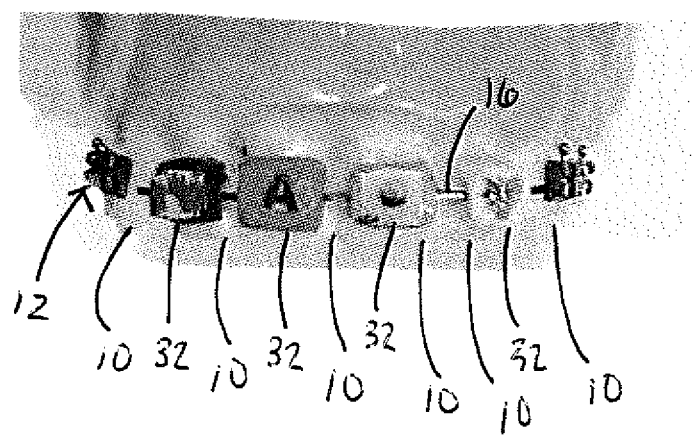
FIG. 4 is a front elevational view of the teeth of FIGS. 1 to 3 with covers secured over dental or orthodontic brackets of the dental braces according to the present invention.
Figure 3:
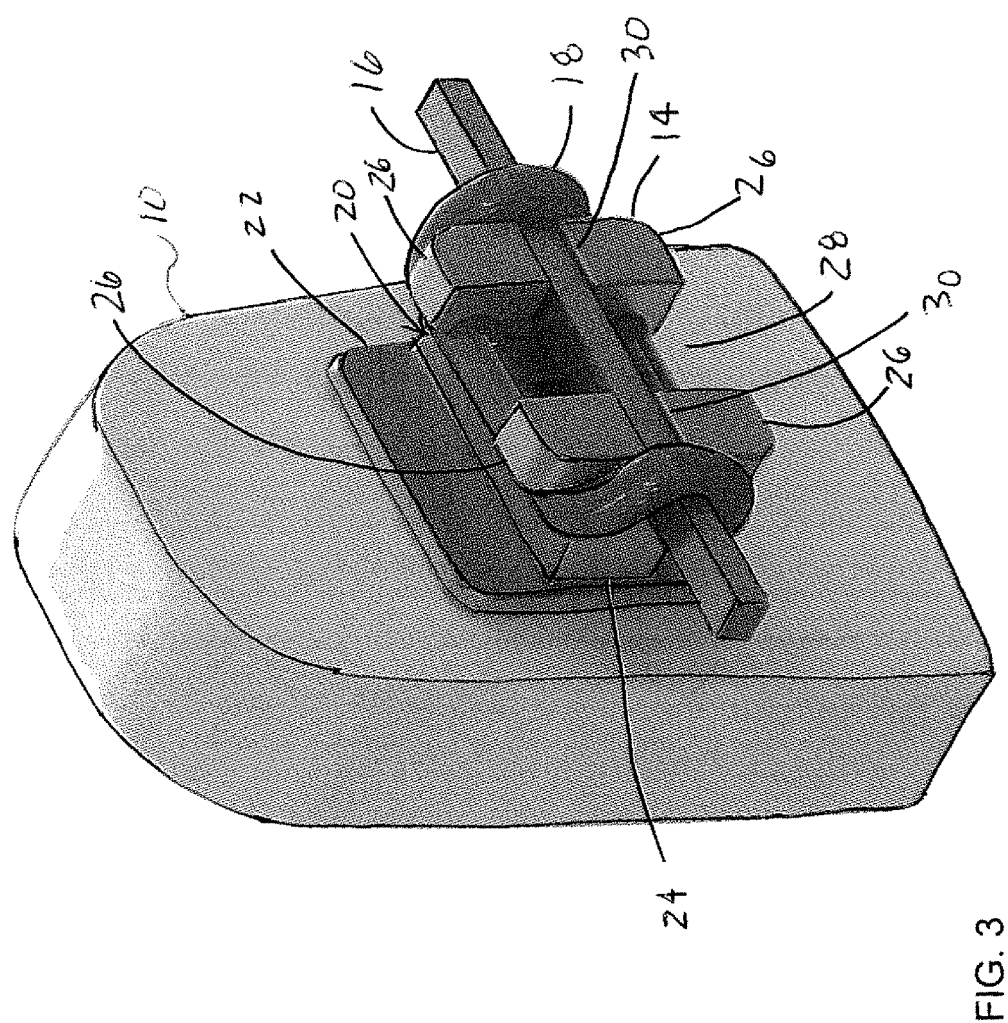
FIG. 3 is an enlarged front perspective view of one of the teeth of FIGS. 1 and 2 with a portion of the dental braces attached thereto.
Figure 5:
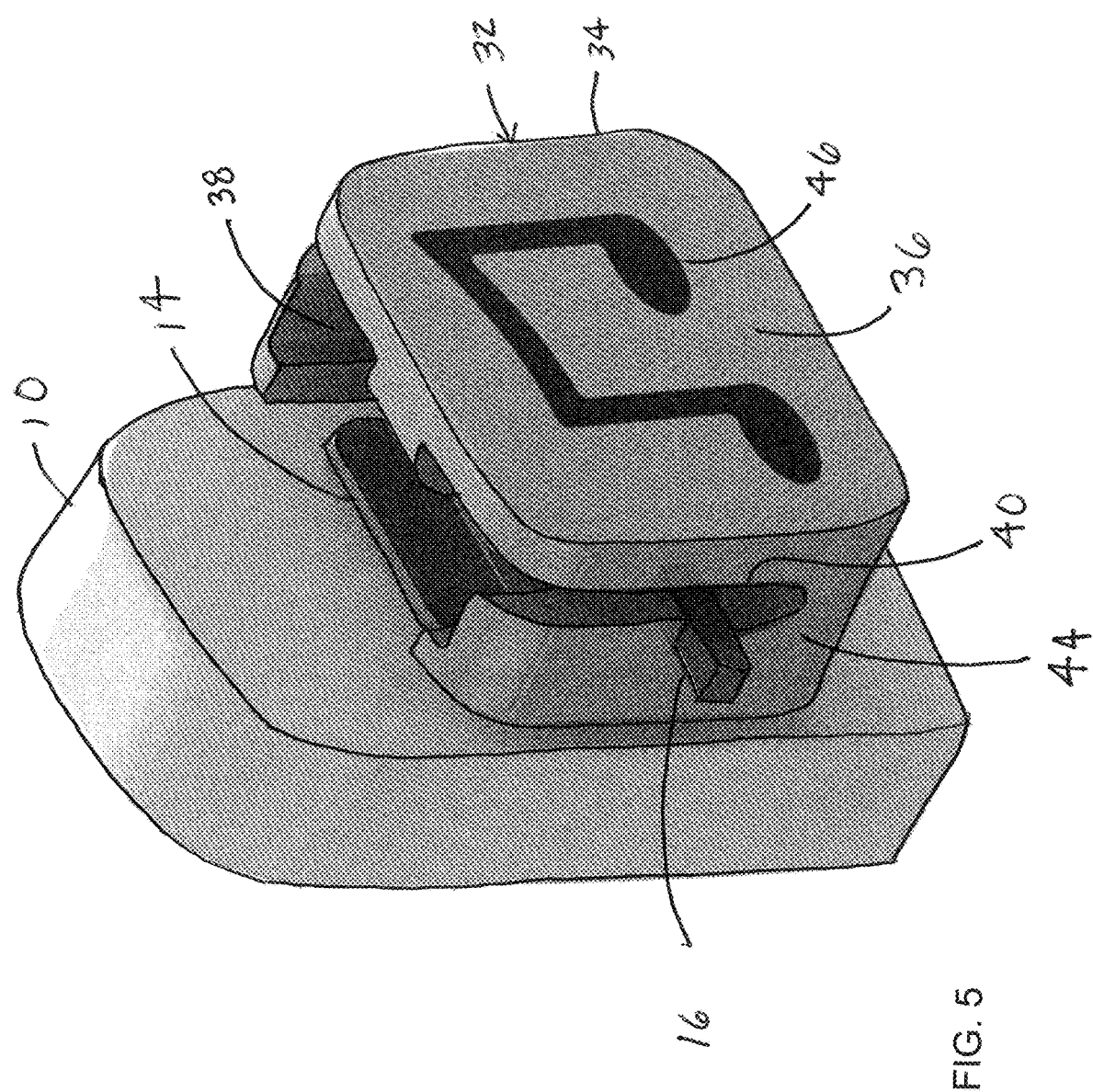
FIG. 5 is an enlarged perspective view of the tooth of FIG. 3 but with one of the covers secured over the orthodontic bracket of the dental braces.
Figure 6:
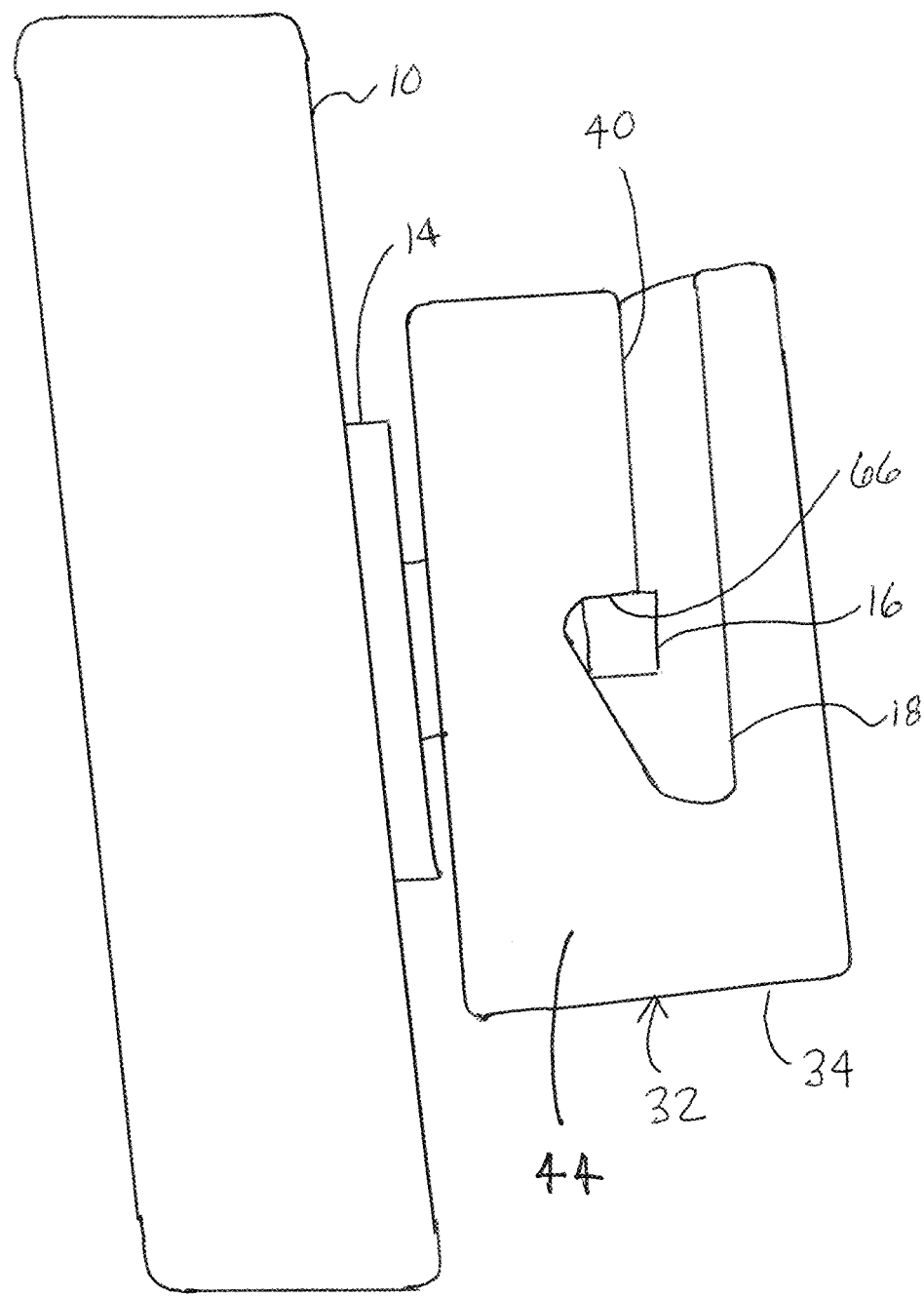
FIG. 6 is a side perspective view of the tooth and the bracket cover of FIG. 5.
Figure 7:
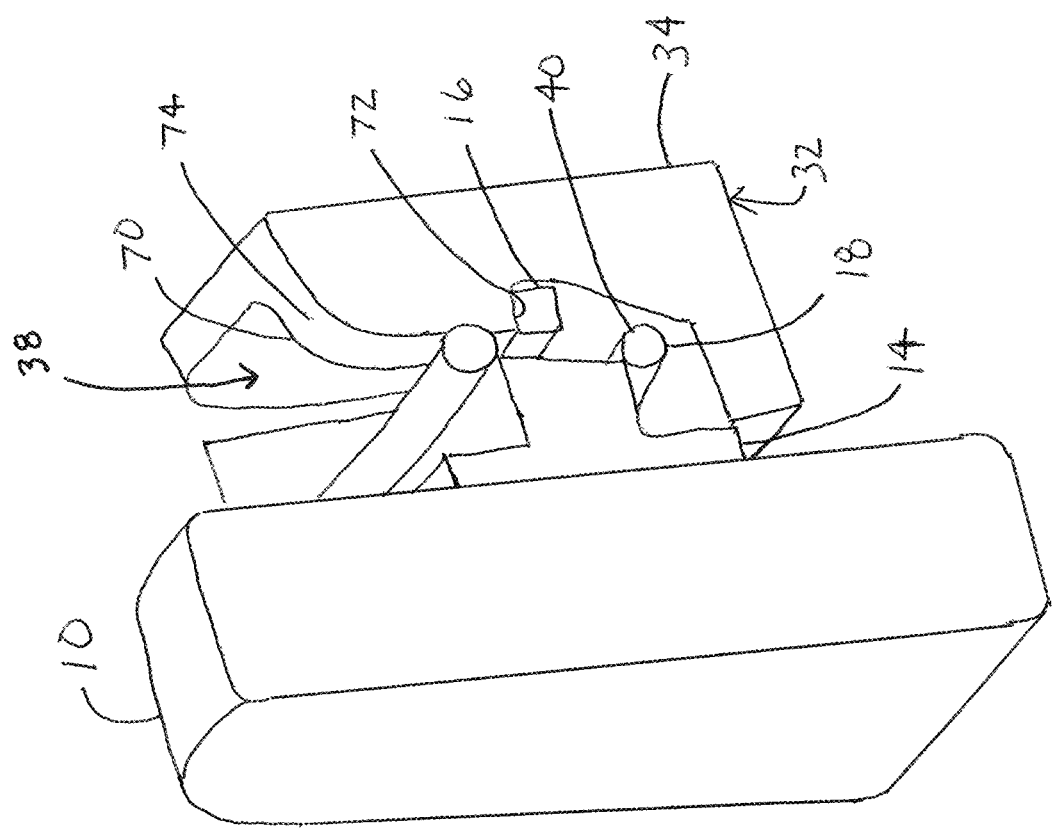
FIG. 7 is a side perspective view, in cross-section, of the tooth and the bracket cover of FIGS. 5 and 6.

FIGS. 1 to 3 illustrate a plurality of teeth 10 having dental or orthodontic braces 12 secured thereto. The illustrated dental braces 12 include a plurality of dental or orthodontic brackets 14 with each of the orthodontic brackets 14 secured to a different one of the teeth 10, bonding material for securing the orthodontic brackets 14 to the front surface of the teeth 10, a retaining or arch wire 16 attached to each of the orthodontic brackets 14, and a plurality of ligatures 18 attaching the arch wire 16 to the orthodontic brackets 14. It is noted that the dental braces 12 can alternatively have any another suitable configuration.

The illustrated orthodontic brackets 14 each include a bracket body 20 and a pad 22. The bracket body 20 and the pad 22 are typically made separately and then connected by welding, brazing, bonding, and the like, but the bracket body 20 and the pad 22 can be formed as an integral one-piece component. The pad 22 is sized and shaped to conform to the front surface of the tooth 10 and the illustrated pad 22 has a rearward-facing surface that is concave for contacting the tooth 10. The illustrated pad 22 is generally rectangular shaped but any other suitable shape can alternatively be utilized. The bracket body 20 extends from the forward-facing surface of the pad 22 and provides guiding structure for the arch wire 16. The illustrated bracket body 20 has a generally rectangular shaped base 24 with opposed left and right lateral sides and opposed top and bottom sides connecting the left and right lateral sides. A rear side of the bracket body 20 faces the forward side of the pad 22. The illustrated bracket body 20 also includes first and second pairs of tie wings 26 forwardly-extending from a front side of the bracket body base 24 and laterally spaced-apart to form a forward facing recess 26 therebetween. The first or left pair of tie wings 26 is located at the left lateral side of the bracket body 20 and the second or right pair of tie wings 26 is located at the right lateral side of the bracket body 20. Each pair of tie wings 26 includes an upper tie wing 26 having an upwardly-extending extension that extends above the top side of the bracket body base 24 and a lower tie wing 26 having a downwardly-extending extension that extends below the bottom side of the bracket body base 24. Each of the illustrated extensions has a concave rearward side which forms a hook that retains the ligature 18 as described in more detail hereinbelow. The bracket body 20 also includes a laterally-extending and forward-facing groove 30 for receiving the arch wire 16 therein at a forward side of the bracket body 20. The illustrated groove 30 extends between the upper and lower tie wings 26 so that the arch wire 16 passes through a left portion of the groove 30 at the first or left pair of tie wings 26, through the recess 28, and through a right portion of the groove 30 at the second or right pair of tie wings 26, where the left and right portions of the groove 30 are laterally spaced-apart by the recess 28. The illustrated orthodontic brackets 14 are formed of a metal such as, for example, stainless steel, titanium, and the like but it is noted that the orthodontic brackets 14 can alternatively be formed of any other suitable material or combination of material. It is also noted that the orthodontic brackets 14 can alternatively have any other suitable configuration.

The bonding material such as, for example, an adhesive is applied to the concave rearward surface of the pad 22 for facilitating a bond between the orthodontic bracket 14 and the tooth 10. It is noted that the bonding material can be of any suitable type and the orthodontic brackets 14 can be alternatively secured to the teeth in any other suitable manner.

The illustrated arch wire 16 goes around the orthodontic brackets 14 and through the forward-facing grooves 30 in the orthodontic brackets 14 to pressure the orthodontic brackets 14 and the teeth 10 to move and align the teeth 10 according to the expert manipulations of the dentist. The illustrated arch wire 16 is a small cross-section resilient wire having a square cross-section but it is noted that the arch wire 16 can alternatively have any other cross-section such as, for example circular. The illustrated arch wire 16 is formed of a metal such as, for example, stainless steel, titanium, and the like but it is noted that the arch wire 16 can alternatively be formed of any other suitable material. It is also noted that the arch wire 16 can alternatively have any other suitable configuration.

The illustrated ligatures 18 secure or attach the arch wire 16 to the orthodontic brackets 14. The illustrated ligatures 18 are elastic bands or O-rings such as, for example, synthetic rubber bands or O-rings but it is noted that the bands can alternatively be formed of any other suitable material. The band extends over a forward side of the arch wire 16 at each lateral side of the orthodontic bracket 14 and extends behind each of the four tie wings 26 to provide a resilient force onto the arch wire 16 in the rearward direction for holding the arch wire 16 within the groove 30. It is noted that the ligatures 18 can alternatively have any other suitable configuration, such as, for example, metal wire.

Figure 8:
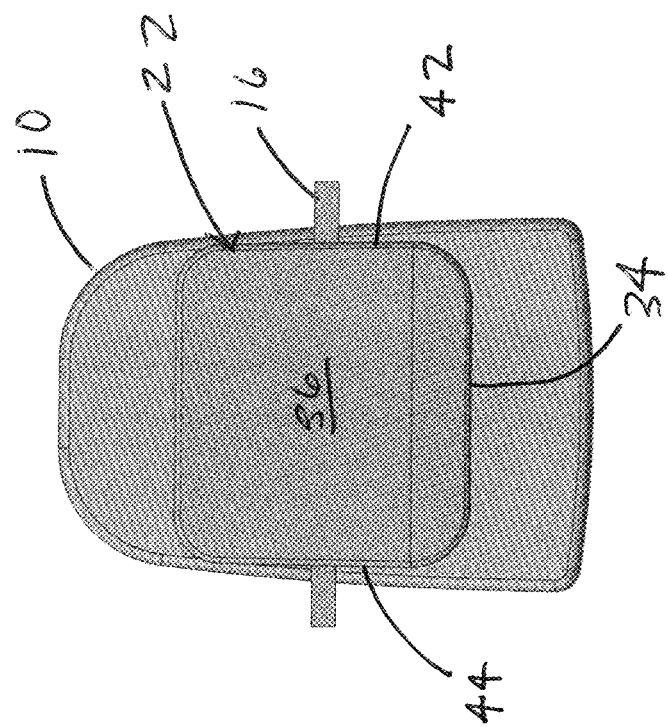
FIG. 8 is a front elevational view of the tooth and the bracket cover of FIGS. 5 to 7.
Figure 9:
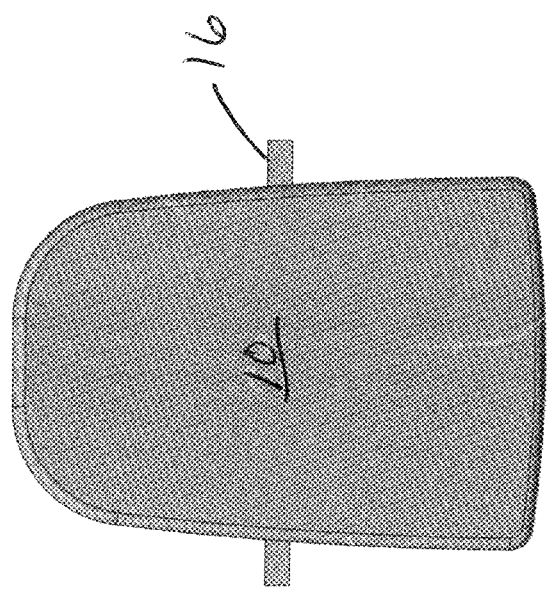
FIG. 9 is a rear elevational view of the tooth and the bracket cover of FIGS. 5 to 8.
Figure 10:
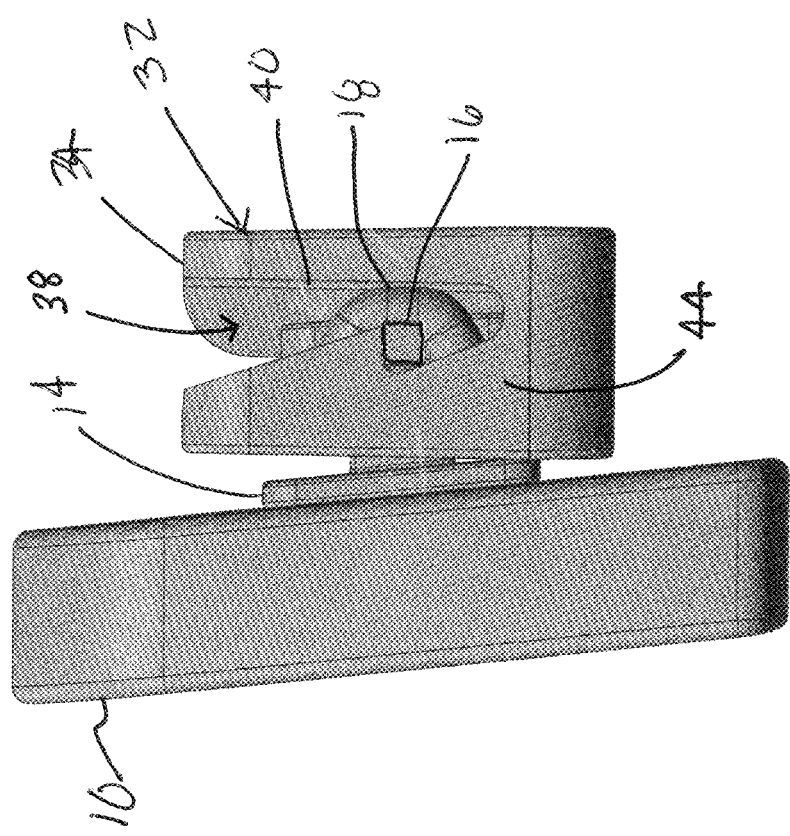
FIG. 10 is a right-side elevational view of the tooth and the bracket cover of FIGS. 5 to 9.
Figure 11:
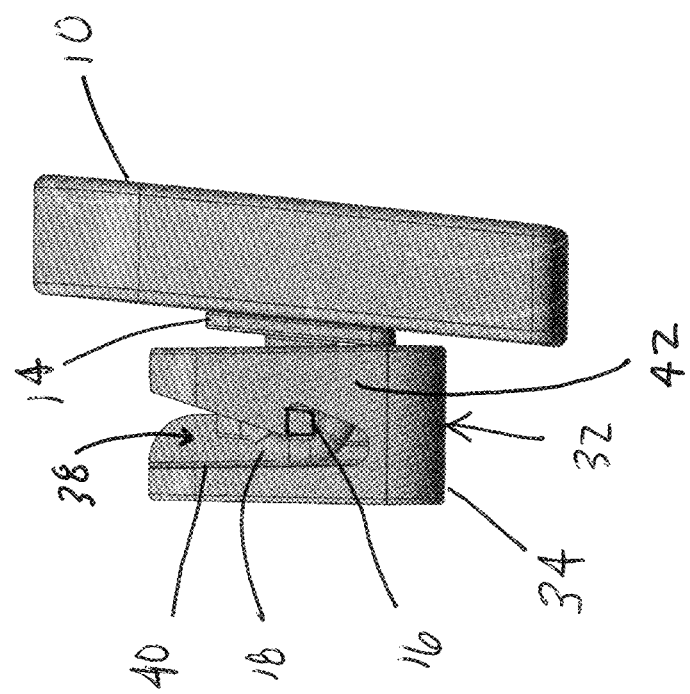
FIG. 11 is a left-side elevational view of the tooth and the bracket cover of FIGS. 5 to 10.
Figure 12:
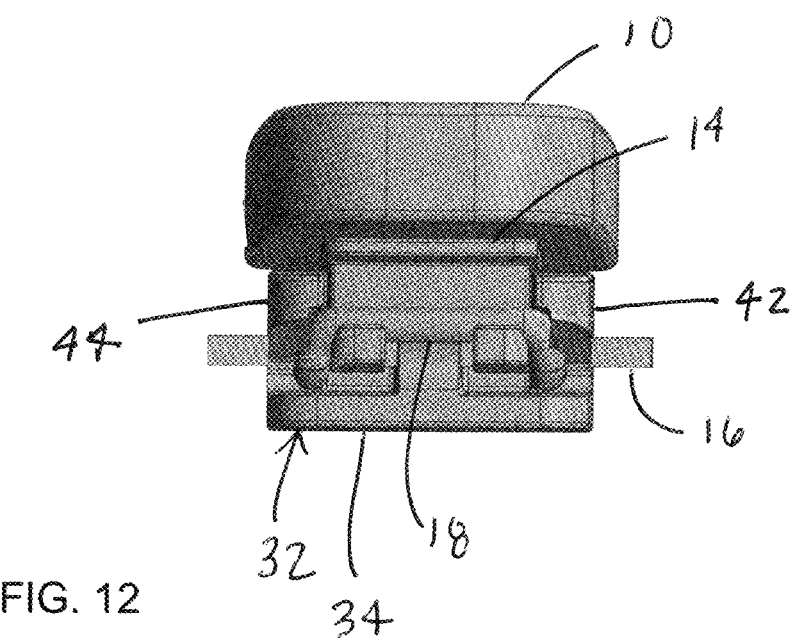
FIG. 12 is a top plan view of the tooth and the bracket cover of FIGS. 5 to 11.
Figure 13:
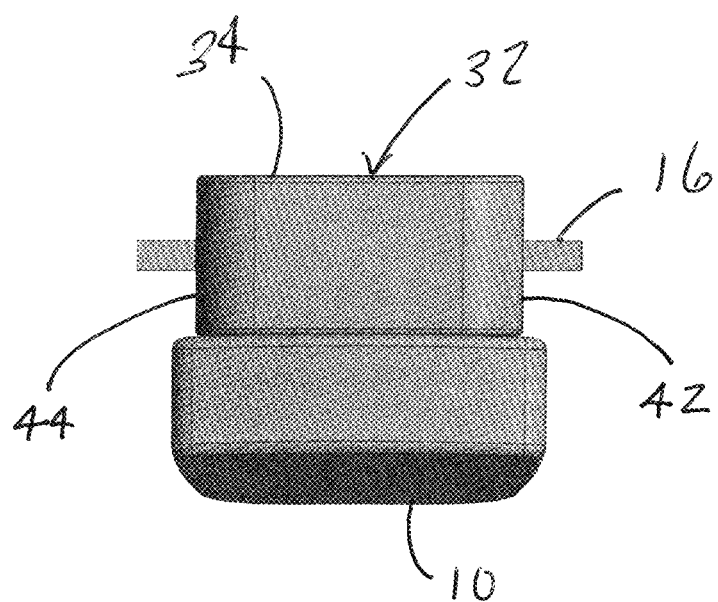
FIG. 13 is a bottom plan view of the tooth and the bracket cover of FIGS. 5 to 12.
Figure 14:
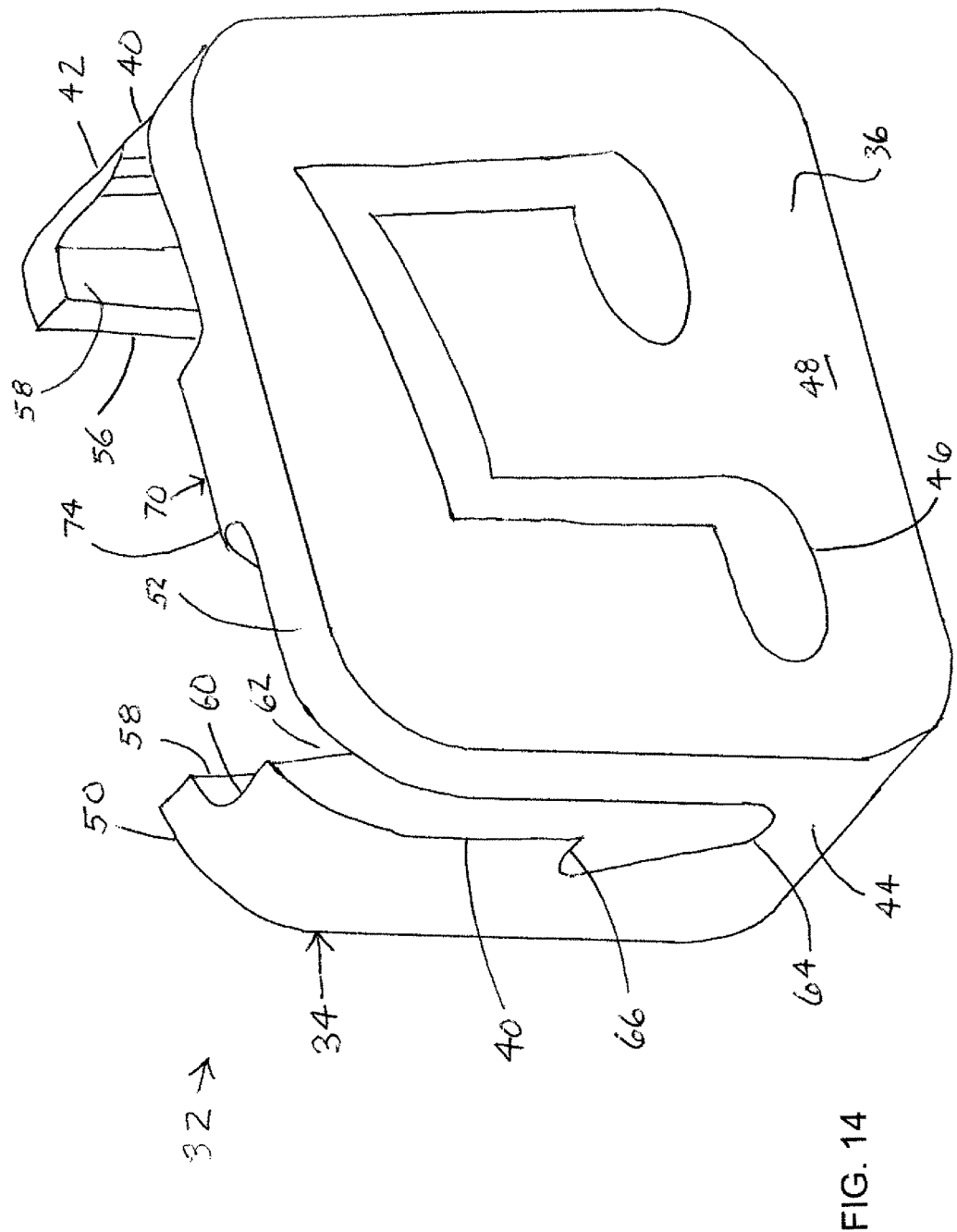
FIG. 14 is an enlarged front elevational view of the bracket cover of FIGS. 5 to 13.
Figure 15:
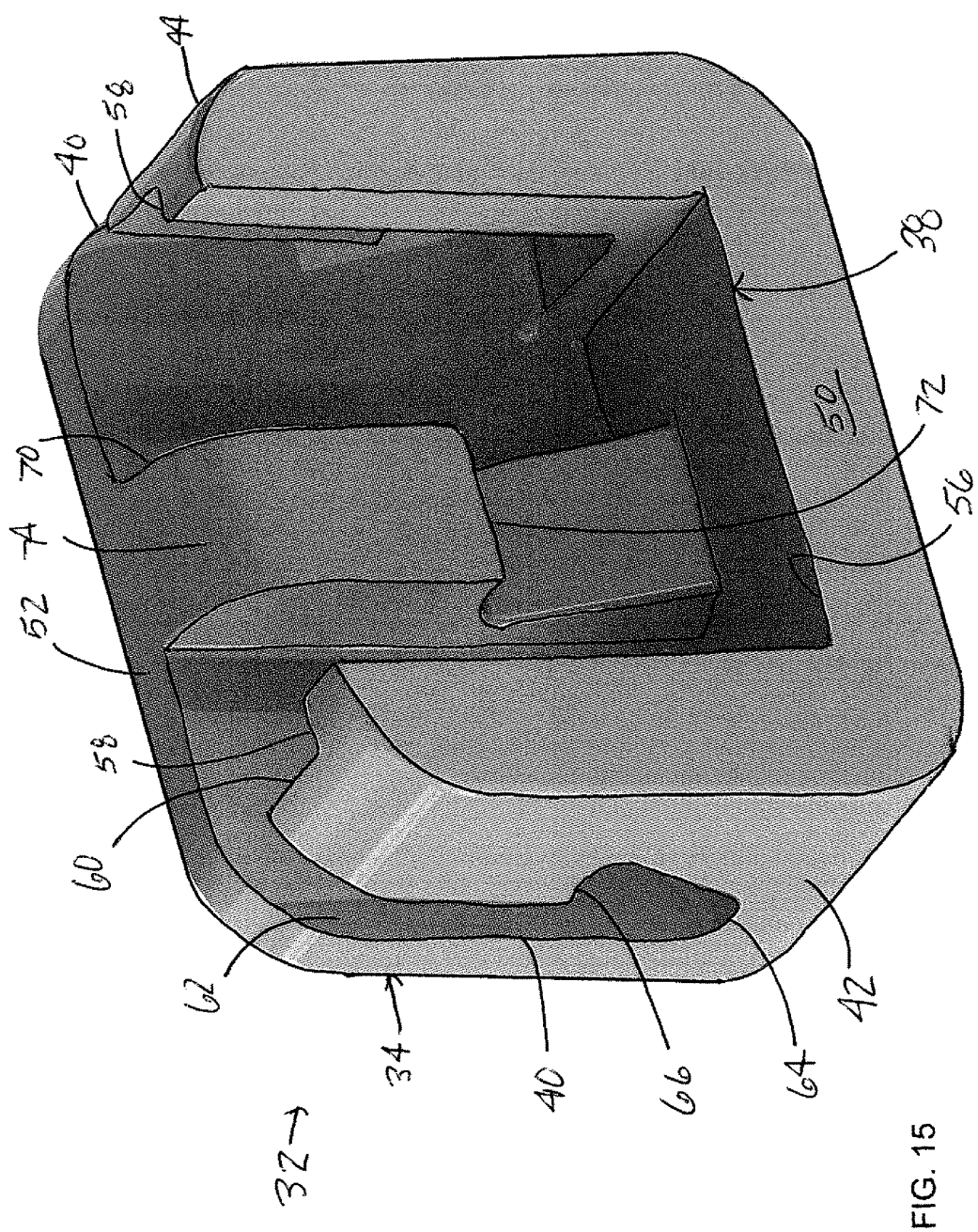
FIG. 15 is a rear perspective view of the bracket cover of FIG. 14.
Figure 16:
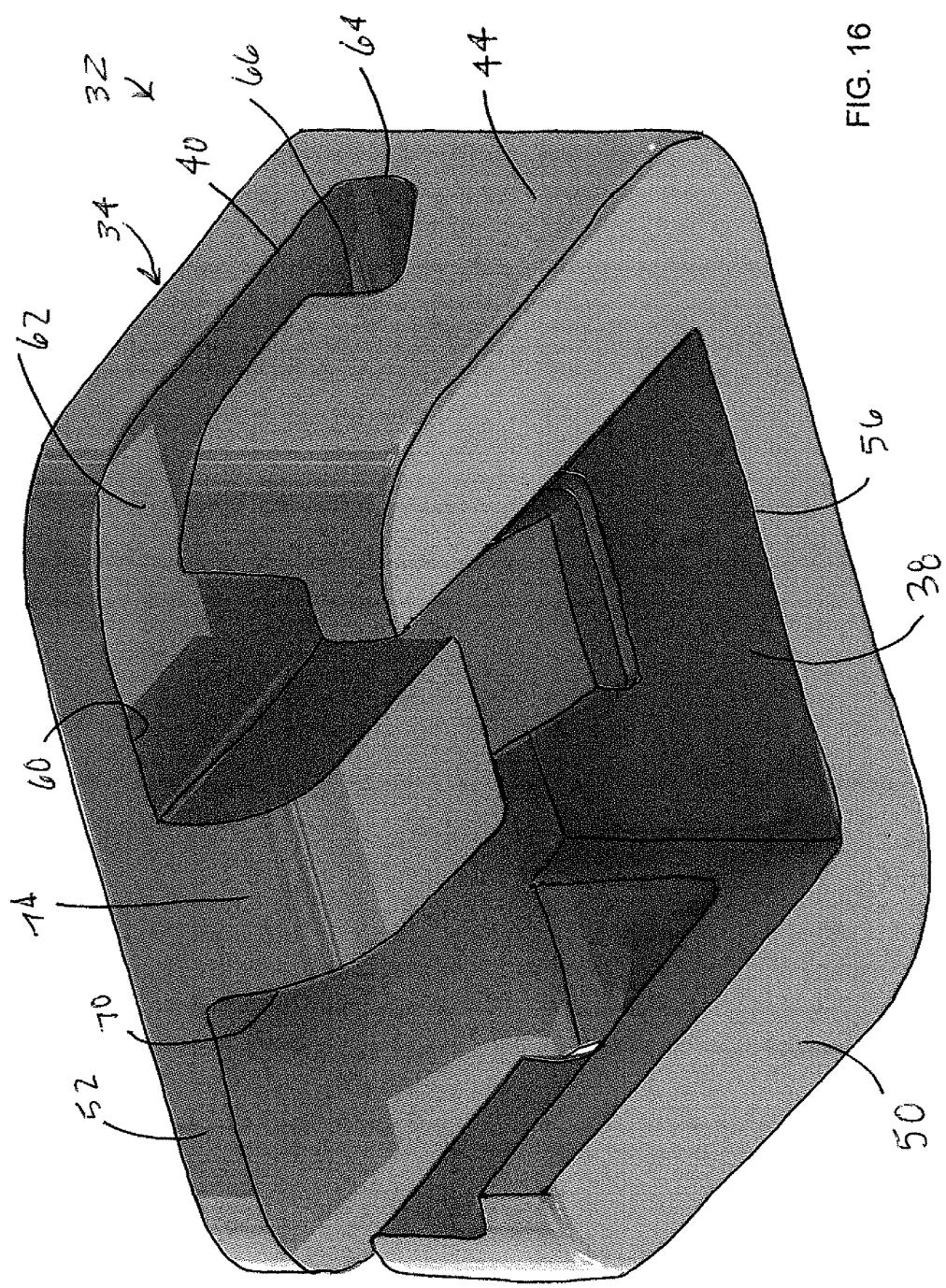
FIG. 16 is another rear perspective view of the bracket cover of FIGS. 14 and 15.
Figure 17:
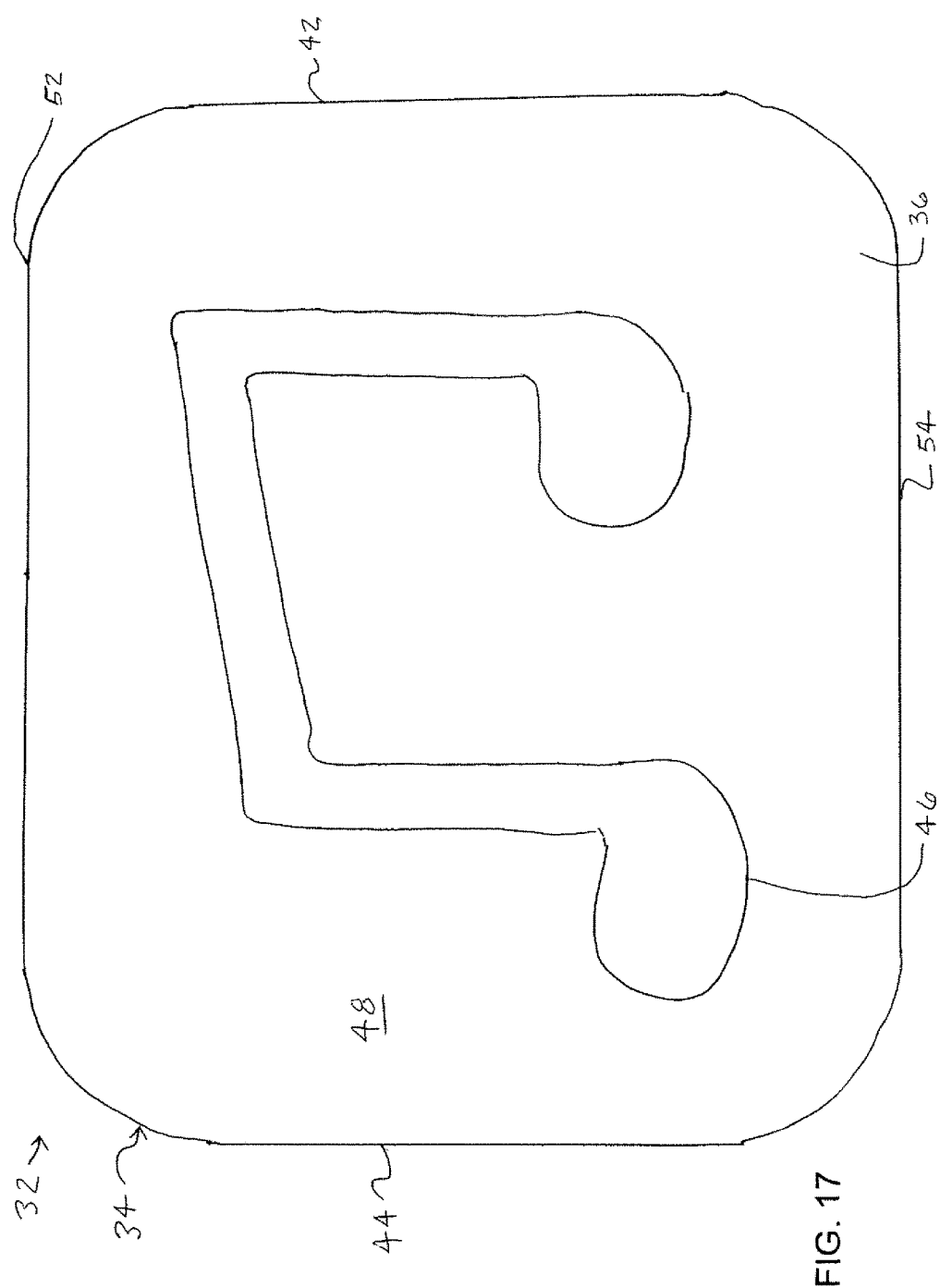
FIG. 17 is a front elevational view of the bracket cover of FIGS. 15 to 16.
Figure 18:
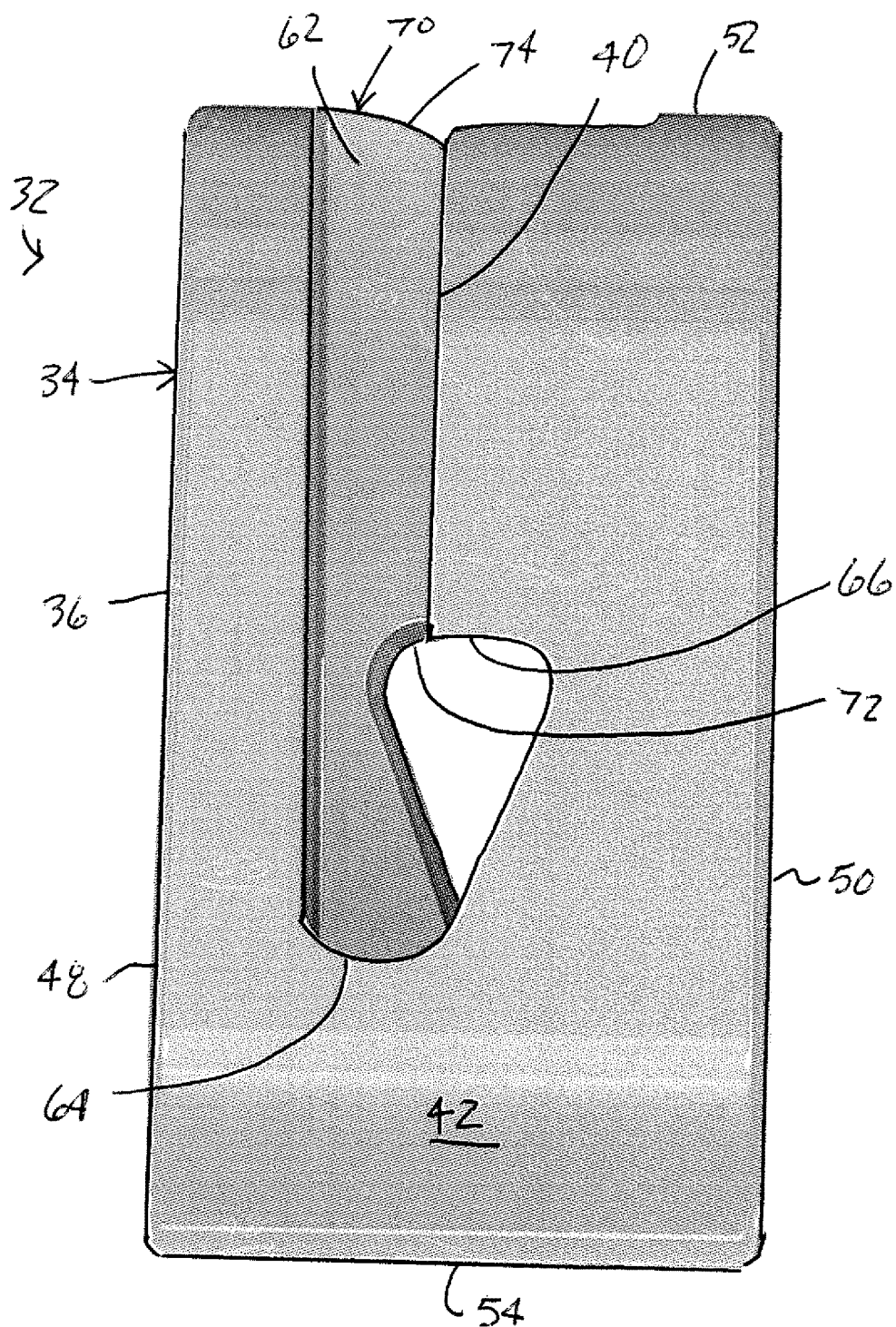
FIG. 18 is a left-side elevational view of the bracket cover of FIGS. 15 to 17.
Figure 19:
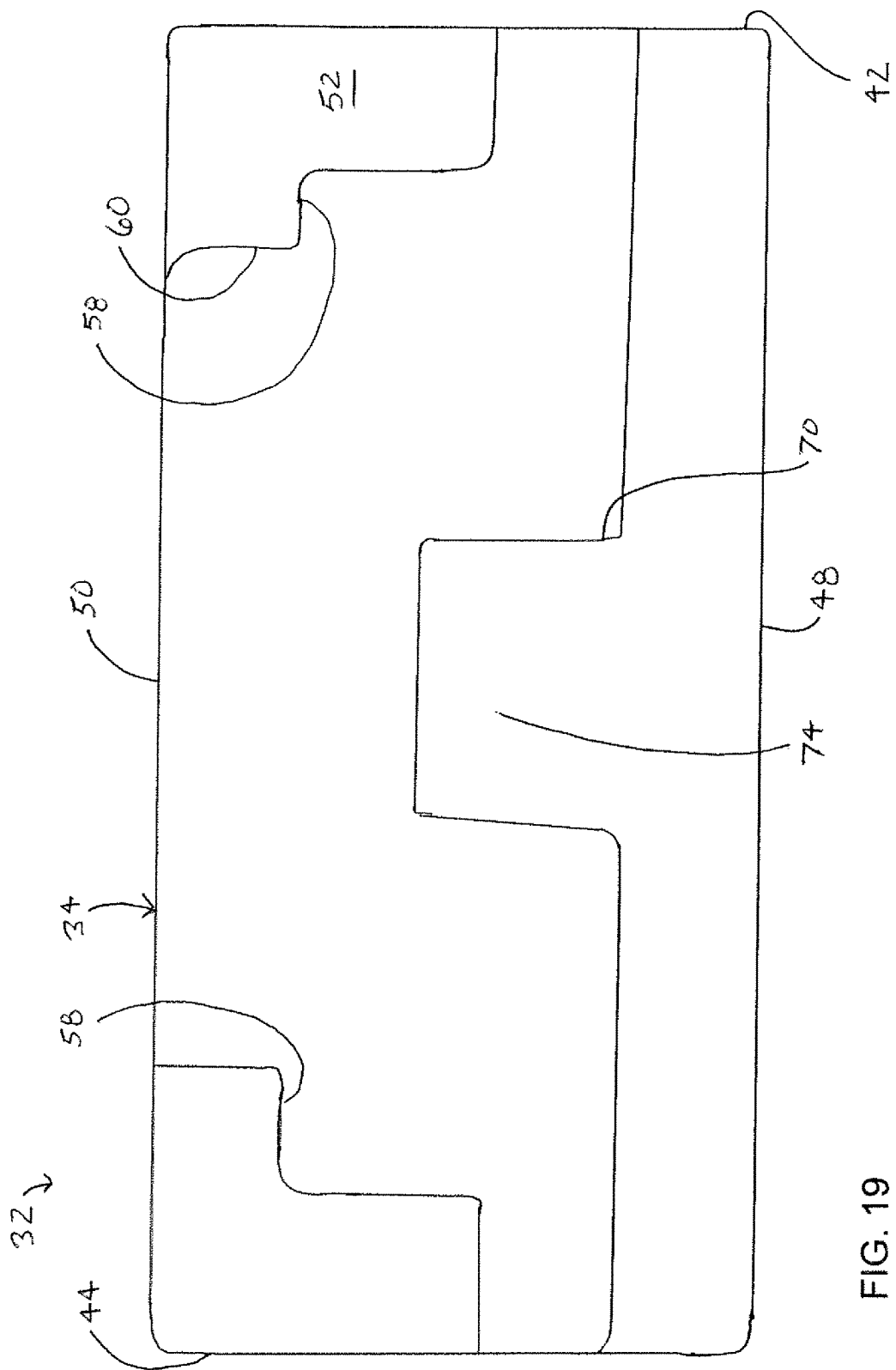
FIG. 19 is a top plan view of the bracket cover of FIGS. 15 to 18.

FIGS. 4 to 13 illustrate covers 32 positioned over the front the orthodontic brackets 14 according to the present invention. It is noted that while the illustrated embodiment shows four of the covers 32 being utilized, it is noted that one or more of the covers 32 can be utilized as desired. The illustrated cover 32 includes a cover body 34 having a forward-facing planar surface 36 and a rearward-facing recess 38 configured for at least partially receiving the orthodontic bracket 14 therein. The illustrated cover body 34 includes first and second slots 40 located on opposed left and right lateral sides 42, 44 of the cover body 34 and each configured so that the arch wire 16 passes laterally through the first and second slots 40 and the recess 38 therebetween. The illustrated forward-facing surface 36 of the cover body 34 is substantially planar and is provided with decorative indicia 46 thereon. FIGS. 8 and 9 show a front elevational view and a rear elevational view respectively of the tooth and the bracket cover.

FIGS. 14 to 19 show the illustrated cover 32 which includes the generally rectangular-shaped cover body 34. The cover body 34 includes opposed front and rear sides 48, 50, opposed top and bottom sides 52, 54 connecting the front and rear sides 48, 50, and the opposed left and right lateral sides 42, 44 connecting the front and rear sides 48, 50 and the top and bottom sides 52, 54. The illustrated front and rear sides 48, 50 are each substantially planar and parallel with one another. The illustrated top and bottom sides 52, 54 are each substantially planar, parallel with one another, and perpendicular to the front and rear sides 48, 50. The illustrated left and right lateral sides 42, 44 are each substantially planar, parallel with one another, perpendicular to the front and rear sides 48, 50, and perpendicular with the top and bottom sides 52, 54. The illustrated intersections or corners between the top and bottom sides 52, 54 and the left and right lateral sides 42, 44 are rounded or provided with a radius. It is noted that the cover body 34 can alternatively have any other suitable shape and/or configuration.

The illustrated front side 48 of the cover body 34 forms the planar forward-facing surface 36 that is provided with the decorative indicia thereon 46. The illustrated decorative indicia 46 is in the form of a "musical single bar note" but it is noted that decorative indicia 46 can alternatively be any other suitable indicia such as, for example, alphabetic letter, numbers, words, names, symbols, logos, images, etc. The decorative indicia 46 can be printed onto the forward-facing surface 36 with ink and the like or can be provided in any other suitable manner. While the illustrated forward-facing surface 36 is planar, it is noted that the forward-facing surface 36 can alternatively have any other suitable shape.

The illustrated rear side 50 of the cover body 34 has a rear opening 56 that forms the opening to the rearward-facing recess 38 that is configured for at least partially receiving the orthodontic bracket 14 therein so that the cover 32 covers or surrounds at least the front of the orthodontic bracket 14 and the ligature 18 secured thereto. The illustrated recess 38 is configured to receive both the bracket body 20 and the ligature 18 therein (best seen in FIG. 12). An inner or forward portion of the recess 38 is sized and shaped for holding a forward portion of the bracket body 20, a portion of the arch wire 16, and the ligature 18 therein and an outer or rearward portion of the recess 38 is sized and shaped to permit a rearward portion of the bracket body 20 to extend therethrough. The illustrated inner or forward portion of the bracket body 20 has lateral width greater than a lateral width of the outer or rearward portion of the recess 38. Thus, the bracket body 20 with the arch wire 16 and the ligature 18 secured thereto cannot be horizontally inserted into the recess 38 through the rear opening 56 formed in the rear side 50 of the cover body 34. When the bracket body 20 with the arch wire 16 and the ligature 18 secured thereto are located within the recess 38, forward-facing abutments 58 formed at the interface between the inner and outer portions of the recess 38 prevent forward removal of the cover 32 from the orthodontic bracket 14 because the bracket body 20 with the arch wire 16 and the ligature 18 secured thereto cannot pass through the rear opening 56 in the rear side 50 of the cover body 34 without deforming the rear side 50 of the cover 32. Thus, the illustrated abutments limit forward movement of the cover 32 relative to the bracket body 20. The forward side of the illustrated recess 38 is closed to limit rearward movement of the cover 32 relative to the bracket body 20.

The illustrated top side 52 of the cover body 34 has a top opening 60 formed therein that opens into the recess 38. The illustrated top opening 60 is sized and shaped so that the bracket body 20 with the arch wire 16 and the ligature 18 secured thereto can pass through the top opening 60 in the top side 52 and into the recess 38 without deforming the top side 52 of the cover body 34 (best seen in FIG. 12). The illustrated bottom side 54 of the over body 34 is not provided with any openings (best seen in FIG. 13) and the bottom side of the recess 38 is closed to limit upward movement of the cover 32 relative to the bracket body 20.

The illustrated left and right lateral sides 42, 44 of the cover body 34 have the first or left slot 40 and a second or right slot 40 respectively. The illustrated first and second slots 40 open into the recess 38 and are configured so that the arch wire 16 passes laterally through the first and second slots 40 and the recess 38 therebetween when the bracket body 20 with the arch wire 16 and the ligature 18 secured thereto are located within the recess 38 (best seen in FIG. 12). The illustrated first and second slots 40 have identical shapes and each extend in the vertical direction from an upper or open end 62 at a top edge of the lateral side 42, 44 to a lower or closed end 64 spaced above a bottom edge of the lateral side 42, 44. Configured in this manner the arch wire 16 can move into and out of the first and second slots 40 through the upper or open ends 62 when the cover 32 is moved on and off of the orthodontic bracket 14 by vertically passing the bracket body 14 with the arch wire 16 and the ligature 18 secured thereto into and out of the recess 38 through the top opening 60 in the top side 52 of the cover body 34. The illustrated first and second slots 40 each have a downward-facing planar abutment 66, that is, facing away from the open end 62, which is configured to engage the arch wire 16 when the arch wire 16 is in the first and second slots 40 while the bracket body 20 with the arch wire 16 and the ligature 18 secured thereto are located within the recess 38. Thus, when the cover 32 is over the orthodontic bracket 14, the abutments 66 resist downward movement of the cover body 34 relative to the bracket body 20 and the arch wire 16 and movement of the arch wire 16 out of the first and second slots 40. The illustrated abutments 66 are located between the upper or open ends 62 and the lower or closed ends 64 and are formed at a rear side of the first and second slots 40. The illustrated first and second slots 40 have enlarged portions 68 located below and adjacent to the abutments 66. It is noted that the first and second slots 40 can alternatively have any other suitable configuration.

The illustrated recess 38 of the cover body 30 is also provided with a projection 70 rearwardly extending within the recess 38 from a forward side of the recess 38. The illustrated projection 70 forms a downward-facing planar central abutment 72 that is centrally located between the abutments 66 of the first and second slots 40 in the lateral direction. The central abutment 72 is configured to engage the arch wire 16 in addition to the slot abutments 66 when the arch wire 16 is in the first and second slots 40 while the bracket body 20 with the arch wire 16 and the ligature 18 secured thereto are located within the recess 38. Thus, when the cover 32 is over the orthodontic bracket 14, the central abutment 72 further resists downward movement of the cover body 34 relative to the bracket body 20 and the arch wire 16. The upper end 74 of the illustrated projection 70 is rounded in the forward/rearward direction to aid in the insertion of the arch wire 6 past the projection in a camming-like manner. It is noted that the central abutment 72 can alternatively have any other suitable configuration.

The illustrated cover body 34 is formed of a resilient material such as a resilient plastic or rubber material so that the cover body 34 can be resiliently flexed as desired when the cover 32 is moved over and off of the orthodontic bracket 14. Preferably the resilient material is available in a relatively large number of colors. It is noted, however, that the cover body 34 can alternatively be formed of any other suitable material.

To install the illustrated cover 32 over the orthodontic bracket 14, the cover 32 is positioned below the bracket body 20 and is vertically moved up over the orthodontic bracket 14 with the arch wire 16 and the ligature 18 secured thereto. As the cover 32 is moved vertically up, the bracket body 20 enters the recess 38 through the top opening 60 in the top side 52 of the cover body 34. As the bracket body 20 enters the recess 34 through the top opening 60 of the cover body 34, the front side 48 of the cover body 34 is resiliently deformed in the forward direction so that the arch wire 16 can pass the central projection 72 until the arch wire 16 is below the downwardly-facing central abutment 72 formed by the projection 70 and the rear side 50 of the cover body 34 is resiliently deformed in a rearward direction so that the arch wire 16 can pass down the first and second slots 40 until the arch wire 16 is below the downwardly-facing abutments 66 formed by the first and second slots 40. Once the bracket body 20 with the arch wire 16 and the ligature 18 attached thereto is located within the recess 38 with the arch wire 16 below the abutments 66, 72, the cover body 34 is released so that it resiliently returns to its un-deformed shape. Positioned in this manner, the cover 32 generally surrounds the bracket body 20 and the ligature 18 and a portion of the arch wire 16 located at the bracket body 20 and is retained over the orthodontic bracket 14 by engagement of the abutments 66, 72 with the arch wire 16 unless adequate force is supplied to resiliently deform the cover 32 in a manner that moves the abutments 66, 72 out of engagement with the arch wire 16. It is noted that the illustrated cover 32 is configured so that the cover 32 does not bind movement of the arch wire 16 relative to the orthodontic bracket 14, does not secure the arch wire 16 to the orthodontic bracket 14 (ligatures, self-ligating brackets, and/or other retainers/inserts are still required to secure the arch wire 16 to the orthodontic brackets 14), and does not otherwise alter the functioning of the dental braces 12 in any way.

To remove the illustrated cover 32 from the orthodontic bracket 14, the cover 32 is vertically moved down off the orthodontic bracket 14 while the arch wire 16 and the ligature 18 remain secured thereto. To move the cover 32 down, the front side 48 of the cover body 34 is resiliently deformed in the forward direction so that the arch wire 16 can pass the projection 70 until the arch wire 16 is above the downwardly-facing central abutment 72 formed by the projection 70 and the rear side 50 of the cover body 34 is resiliently deformed in a rearward direction so that the arch wire 16 can move above the downwardly-facing abutments 66 formed by the first and second slots 40. Once the bracket body 20 with the arch wire 16 and the ligature 18 attached thereto exit the recess 38 through the top opening 60 and the upper or open ends 62 of the first and second slots 40, the cover body 34 is released so that the cover body 34 resiliently returns to its un-deformed shape.

Any of the features or attributes of the above-described embodiments and variations can be used in combination with any of the other features and attributes of the above-described embodiments and variations as desired.

From the foregoing disclosure it will be apparent that the illustrated covers 32 enable wearers of dental braces 12 to express themselves by personalizing and/or decorating their dental braces 12 without binding movement of the arch wire 16 relative to the orthodontic bracket 14, does not secure the arch wire to the orthodontic brackets, and without altering the functioning of the dental braces 12. It is also apparent that the illustrated covers 32 can be mass produced in a manner such that the covers 32 are relatively inexpensive and can thus be utilized in a disposable manner so that the covers 32 can be changed on a regular basis such as, for example, every few days or even every day. It should be further apparent that the illustrated covers 32 provide some level of protection to reduce food and other objects from lodging in the orthodontic brackets 14, the arch wire 16, and/or the ligatures 18.

From the foregoing disclosure and detailed description of certain preferred embodiments, it will be apparent that various modifications, additions and other alternative embodiments are possible without departing from the true scope and spirit of the present invention. The embodiments discussed were chosen and described to provide the best illustration of the principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

What is claimed is:

1. Dental braces comprising, in combination:
   at least one orthodontic bracket for securement to a tooth and having a laterally-extending slot;
   an arch wire extending laterally through the slot of the orthodontic bracket; and
   a cover comprising:
      a body having a forward-facing surface and a rearward-facing recess configured for at least partially receiving the orthodontic bracket therein;
      wherein the body includes first and second vertically extending slots located on opposed lateral sides of the body and each configured so that the arch wire passes through the first and second slots and recess of the body and so that the first and second slots directly secure the body to the arch wire adjacent opposed sides of the orthodontic bracket;
      wherein the first and second vertically extending slots each have an open top end and a closed bottom end so that upward movement of the body relative to the orthodontic bracket enables the arch wire to enter the vertically extending slots;
      a projection rearwardly-extending within the recess from a forward side of the recess, the projection forming a downward-facing abutment centrally located between the first and second vertically extending slots in a lateral direction, the downward facing abutment configured to engage the arch wire within the recess of the body when the body is over the orthodontic bracket and the arch wire passes laterally through the first and second vertically extending slots so that the downward-facing abutment resists downward movement of the body relative to the orthodontic bracket and the arch wire; and
      wherein the body is formed of one of a resilient plastic material and a resilient rubber material so that the body can be resiliently flexed when the body is selectively secured directly to and removed from the arch wire.

2. The dental braces according to claim 1, wherein forward-facing surface is provided with decorative indicia thereon.

3. The dental braces according to claim 1, wherein the cover is configured so that the cover does not bind movement of the arch wire relative to the bracket.

4. The dental braces according to claim 1, wherein the first and second vertically-extending slots each have an abutment facing away from the open top end to engage the arch wire when the arch wire is in the first and second vertically-extending slots and the cover is over the orthodontic bracket and to resist movement of the arch wire out of the first and second vertically-extending slots through the open top ends.

5. The dental braces according to claim 4, wherein the open top ends of the first and second vertically extending slots are located at top edges of the opposed lateral sides of the body and the abutments of the first and second vertically extending slots are downward facing, and wherein a top of the body is provided with an opening for passage of the orthodontic bracket therethrough when the cover is moved vertically over and off of the orthodontic bracket.

6. The dental braces according to claim 1, wherein a top of the body is provided with an opening for passage of the orthodontic bracket therethrough when the cover is moved vertically over and off of the orthodontic bracket.

7. The dental braces according to claim 6, wherein a bottom of the body is closed to prevent passage of the orthodontic bracket therethrough.

8. The cover according to claim 1, wherein an upper end of the projection is rounded in a forward/rearward direction so that the projection moves in a forward direction when the arch wire engages the upper end of the projection as the body is moved upwardly over the orthodontic bracket so that the arch wire can move past the projection.

9. A method of covering an orthodontic bracket having an arch wire laterally extending therethrough, the method comprising the steps of, in combination:
   obtaining a cover comprising:
      a body having a forward-facing surface and a rearward-facing recess configured for at least partially receiving the orthodontic bracket therein;
      wherein the body includes first and second vertically-extending slots located on opposed lateral sides of the body and each configured so that the arch wire passes laterally through the first and second slots and the recess of the body and so that the first and second slots directly secure the body to the arch wire adjacent opposed sides of the orthodontic bracket; and
      wherein the first and second vertically extending slots each have an open top end and a closed bottom end so that upward movement of the body relative to the orthodontic bracket enables the arch wire to enter the vertically extending slots;
      a projection rearwardly-extending within the recess from a forward side of the recess, the projection forming a downward-facing abutment centrally located between the first and second vertically extending slots in a lateral direction, the downward facing abutment configured to engage the arch wire within the recess of the body when the body is over the orthodontic bracket and the arch wire passes laterally through the first and second vertically extending slots so that the downward-facing abutment resists downward movement of the body relative to the orthodontic bracket and the arch wire; and wherein the body is formed of one of a resilient plastic material and a resilient rubber material so that the body can be resiliently flexed when the body is selectively secured directly to and removed from the arch wire; and moving the body over the orthodontic bracket so that the arch wire downwardly moves into the first and second slots to directly secure the body to the arch wire adjacent opposed sides of the orthodontic bracket and the orthodontic bracket is at least partially received in the recess of the body and the cover covers at least a front side of the orthodontic bracket.

10. The method according to claim 9, wherein a top of the body is provided with an opening for passage of the orthodontic bracket therethrough when the cover is moved vertically over and off of the orthodontic bracket.

11. The method according to claim 10, wherein a bottom of the body is closed to prevent passage of the orthodontic bracket therethrough.

12. The cover according to claim 9, wherein an upper end of the projection is rounded in a forward/rearward direction so that the projection moves in a forward direction when the arch wire engages the upper end of the projection as the body is moved upwardly over the orthodontic bracket so that the arch wire can move past the projection.

* * * * *